(12) United States Patent
Owen-Smith (10) Patent No.: US 7,763,440 B2
(45) Date of Patent: Jul. 27, 2010

(54) DIAGNOSIS OF PRE-ECLAMPSIA (76) Inventor: Brian David Owen Owen-Smith, 48 Westgate, Chichester, West Sussex (GB) PO19 3EV ( * ) Notice: Subject to any disclaimer, the term of this patent is extended or adjusted under 35 U.S.C. 154(b) by 886 days.

(21) Appl. No.: 10/560,954

(22) PCT Filed: Jun. 11, 2004

(86) PCT No.: PCT/GB2004/002521

§ 371 (c)(1),
(2), (4) Date: Oct. 9, 2006

(87) PCT Pub. No.: WO2004/113926

PCT Pub. Date: Dec. 29, 2004

(65) Prior Publication Data

US 2007/0020766 A1 Jan. 25, 2007

(30) Foreign Application Priority Data

Jun. 16, 2003 (GB) .................. 0313828.6

(51) Int. Cl.
*C12Q 1/34* (2006.01)
(52) U.S. Cl. .................. 435/18; 435/201; 131/334
(58) Field of Classification Search .................. 435/18
See application file for complete search history.

(56) References Cited

U.S. PATENT DOCUMENTS 5,849,474 A  12/1998  Olson et al.
6,753,159 B1 * 6/2004  Lee .............................. 435/12

FOREIGN PATENT DOCUMENTS

WO      WO 0008207      * 2/2000   .................. 435/12
WO      WO 2004/088324    10/2004

OTHER PUBLICATIONS

Fossati et al., Use of 3,5-Dichloro-2-hydroxybenzenesulfonic acid/ 4-Aminophenazone Chromogenic system in direct enzymatic assay of uric acid in serum and urine, CLincal Chemistry, vol. 26, p. 227-231, 1980.*
Dunlop et al., Plasma urate changes in pre-eclampsia, Bristish Medical Journal, 1978.*
Pipkin, Uric acid, endothelial dysfunctin and pre-eclampsia, Journal of Hypertension, vol. 22, p. 237-239, 2004.*
Schuster et al. Plasma urate measurements and fetal outcome in preeclampsia, Gynecology Obstetrics Invest., vol. 12, 1981 Abstract.*
Chappell et al., "A longitudinal study of biochemical variables in women at risk of preeclampsia," Am J Obstect Gynecol (2002) 187:127-136.
Many et al., "Hyperuricemia and xanthine oxidase in preeclampsia, revisited," Current Development (1996) 174:288-291.
Owen-Smith "Salivary urate in gout, exercise, and diurnal variation," The Lancet (1998) vol. 1, Ip.
Seitchik, "The metabolism of urate in pre-eclampsia". Am. J. Obst. Gynecol., (1956), 72:40-47.
Extract from Rheumatology Medicine (1985), Dieppe et al.
"The management of severe pre-eclampsia/eclampsia" published by the Royal College of Obstetricians and Gynaecologists in Mar. 2006.
Extract from Medical Disorders of Pregnancy (1989) de Swiet (Ed), 2nd edn, Oxford University Press, Mumbai.
Letter from Dr. Jonathon Hooker to Dr Owen-Smith, Dec. 12, 1997.
Typed version of letter from Dr. Jonathon Hooker to Dr Owen-Smith, Dec. 12, 1997.
Extract from Review of Medical Physiology, Ganong (1963), Lange Medical Publications, Los Altos, Californian, illustration on p. 4 captioned "Electrolyte composition of body fluids in mEq/liter".
Sorensen, "The elimination of uric acid in man studied by means of C14 labelled uric acid", J. Clin. Lab. Invest. (1960) 12 (supp. 54):186-194.
Owen-Smith et al., "Diurnal and nocturnal variations of enteral uricolysis during fasting and refeeding" (Abstr), Ann Rheum Dis (1981) 40:523-24.
Xiangwei et al. "Two independent mutational events in the loss of urate oxidase during hominoid evolution", Journal of Molecular Evolution (1992) 34:78-84.
Modena & Fieni, "Amniotic fluid dynamics", Acta Bio Medica Ateneo Parmense (2004) 75; Suppl. 1:11-13).
Connon and Wadesworth, "An Evaluation of Serum Uric Acid Estimations in Toxaemia of Pregnancy", Aust. N. Z. J. Obstet. Gynaec. (1968), 8:197-201.
de Jong et al., "Decrease first trimester uric acid production in future pre-eclamptic patients", J. Perinat. Med. (1997) 25 (4):347-352.

(Continued)

*Primary Examiner*—Jon P Weber
*Assistant Examiner*—Tiffany M Gough
(74) *Attorney, Agent, or Firm*—Pepper Hamilton LLP (57) ABSTRACT

The present invention provides a method for diagnosis of pre-eclampsia which comprises measuring urate in a biological sample. The sample is preferably maternal saliva.

4 Claims, 6 Drawing Sheets

OTHER PUBLICATIONS

Campion et al., "Binding of Urate by Serum Proteins", Arthritis and Rheumatism (1975), 18:747.

Schloss and Crawford, "Metabolism of nitrogen, phosphorus and purin substances in the new-born; with special reference to the causation of uric acid infarcts in the kidney", Arch. Pediatr. Adolesc. Med. (1911) 1(3):203-229.

Slemons & Bogert "The uric acid content of maternal and fetal blood", J Biol Chem (1917) XXXII(1):63-69.

Polycove et al. "Uric acid metabolism: the oxidation of uric acid in normal subjects and patients with gout, polycythemia and Leukemia", Clinical Research Rpoceedings (1957) 38-39.

Gutman A.B., Editorial "Significance of the renal clearance of uric acid in nnormal and gouty man" Am J. Med. (1964) 37(6):833-838.

Redman et al, "Plasma-Urate Measurements in Predicting Fetal Death in Hypertensive Pregnancy" The Lancet (1976) Jun. 26:1370-1373.

Ames et al. "Uric acid provides an antioxidant defence in humans against oxidant- and radical-caused aging and cancer: A hypothesis", Proc. Natl. Acad. Sci. USA (1981) 78(11):6858-6862.

Owen-Smith, "Significance of circadian variations of uric acid elimination", Ann. Rheum. Dis. (1983) 42(Supp.):87.

Owen-Smith et al. "Management of gout and the role of salivary urate" Men's Health Journal (2003) 2(1)6-9.

Les Comptes Rendus de l'Academie de Sciences, Physiological Chemistry.

Simmonds et al "Pregnancy in xanthinuria: Demonstration of fetal uric acid production?" J. Inhe. Metab. Dis., (1984) 7:77-79.

Hakim A & Owen-Smith et al. Salivary urate, a non-invasive method of diagnosing and monitoring gout. Rheum. (2000) 39(Supplement 1):99.

Roberts et al. "Poor pregnancy outcomes linked to increased uric acid" Science Daily, Oct. 29, 2005.

Roberts et al "Uric Acid is as important as Proteinuria in Identifying Fetal risk in women with Gestational Hypertension", Hypertension, (2005)46:1263-1269.

Hill et al., "Diurnal variation of serum urate in pregnancy" British Medical Journal (1977) 2:1520.

NIHR Health Technology Assessment Programme News item "Research investigates tests and interventions for preeclampsia", 1998.

Dunlop et al "The effect of normal pregnancy upon the renal handling of uric acid", Brit J Obstetrics & Gynaecology (1977) vol. 84. pp. 13-21.

Zachau-Christiansen, "The variations in serum uric acid during 24 hours and from day to day", Scanndinav.J.Clin & Lab. Investigation, (1957) 9:244-248.

Hill, "Metabolism of uric acid in normal and toxemic pregnancy", Mayo Clin Proc, (1978) 53:743-751.

Abstract of document 9 presented in Paris, Jun. 1981.

Fox IH, Palella TD, Kelly WM. Hyperuricaemia: A marker for cell energy crisis. N Engl J Med 1987 317, 2, 111-112.

* cited by examiner

DIAGNOSIS OF PRE-ECLAMPSIA

CROSS-REFERENCE TO RELATED APPLICATIONS

This application is the U.S. National Stage filing of International Application Serial No. PCT/GB2004/002521 filed Jun. 11, 2004, which claims priority to GB 0313828.6 filed Jun. 16, 2003, each of which is incorporated herein by reference in its entirety.

This invention relates to detection of pre-eclampsia. In particular, it relates to diagnosis of pre-eclampsia by detecting elevated levels of urate, the sodium salt of uric acid, 2,6,8, trioxypurine, in a biological fluid, saliva.

The invention is a method of using the enhanced sensitivity inherent in urate concentration in saliva, as compared with that of blood, and depends on urate as a metabolic compound with unique and predictable behaviour.

Pre-eclampsia occurs in approximately 2-4% of pregnant women and is a common cause of maternal and fetal mortality and morbidity. In severe cases, early delivery is necessary and there is therefore the risk of the child being handicapped.

Pre-eclampsia, (Toxaemia of pregnancy, Pre-eclamptic toxaemia) otherwise known as 'gestational proteinuric hypertension' (GPH) is a multi-system disease of pregnancy of unknown cause. The maternal syndrome is characterised by various abnormalities: increased blood pressure, oedema, proteinuria and abnormal clotting, liver and renal function. This may lead to multi-system failure, intracranial haemorrhage and fits. The cause of pre-eclampsia is believed to lie in the placenta and there is evidence for a circulating endothelial cell "toxic" factor.

Oxidative stress is believed central to development of pre-eclampsia and associated with poor placental perfusion. Raised blood urate, a marker of oxidative stress, is associated with severity of pre-eclampsia and foetal outcome (Many et al, 1996). Blood urate is also a predictor of pre-eclampsia (Chappell et al 2002).

The symptoms of pre-eclampsia are generally detectable from around 28 weeks up to full term and are not usually apparent before 24 weeks. The conventional tests, as disclosed in the prior art EP 0927355B1 are for kidney failure by measuring urea in the blood or protein in the urine, and for increased maternal blood pressure.

The prior art however fails in several important aspects, blood tests are time consuming, need an experienced operator, may cause physical and psychological discomfort and could lead to dangerous needle stick injuries such as infectious hepatitis or Aids. Blood samples also require specialist storage techniques to arrest decomposition.

What is needed therefore is a method for identification of those pregnant women at risk of or with pre-eclampsia with a biochemical test to detect oxidative stress, that is of high sensitivity, is inexpensive, non-invasive and is both simple and quick to perform routinely or in emergency and is safer, easier, quicker, and cheaper to obtain than blood.

A test for urate is ideal since it is a powerful antioxidant and marker of oxidative stress. Further, biochemical change is likely to occur before irreversible tissue damage. Blood urate concentration is however a poor discriminator of pre-eclampsia as it is also increases in normal pregnancy.

Figure 1:
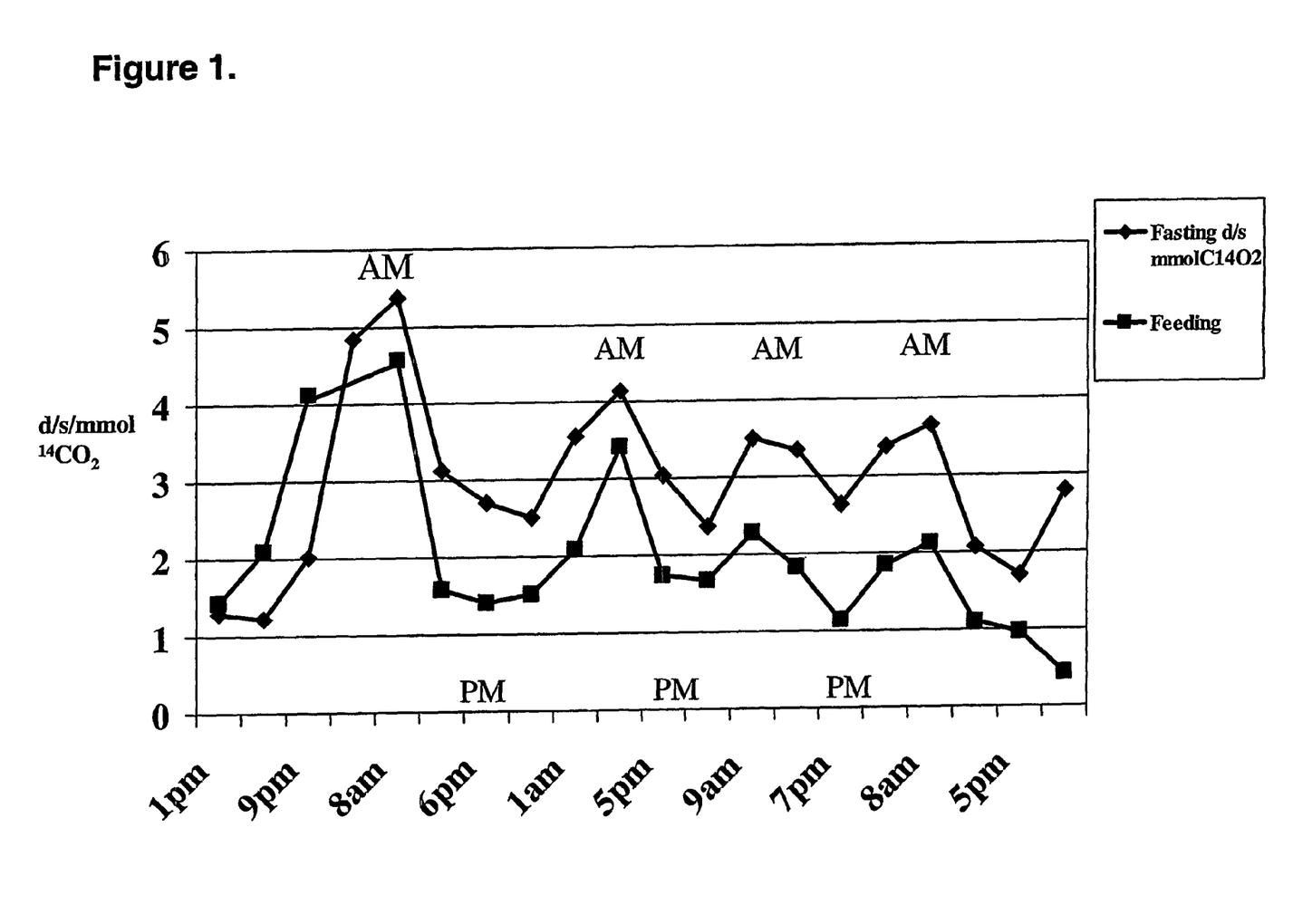
FIG. 1 Daily variation of enteral uricolysis increased at night. Graph of disintegrations/sec/mmol $^{14}CO_2$ derived from uric acid-2-$^{14}$C 200 mg, 36 μCi, in 2 ml of water injected intravenously during (A) 5 days fasting and hyperuricaemic and (B) 5 days whilst normouricaemic on a low purine diet.
Figure 2:
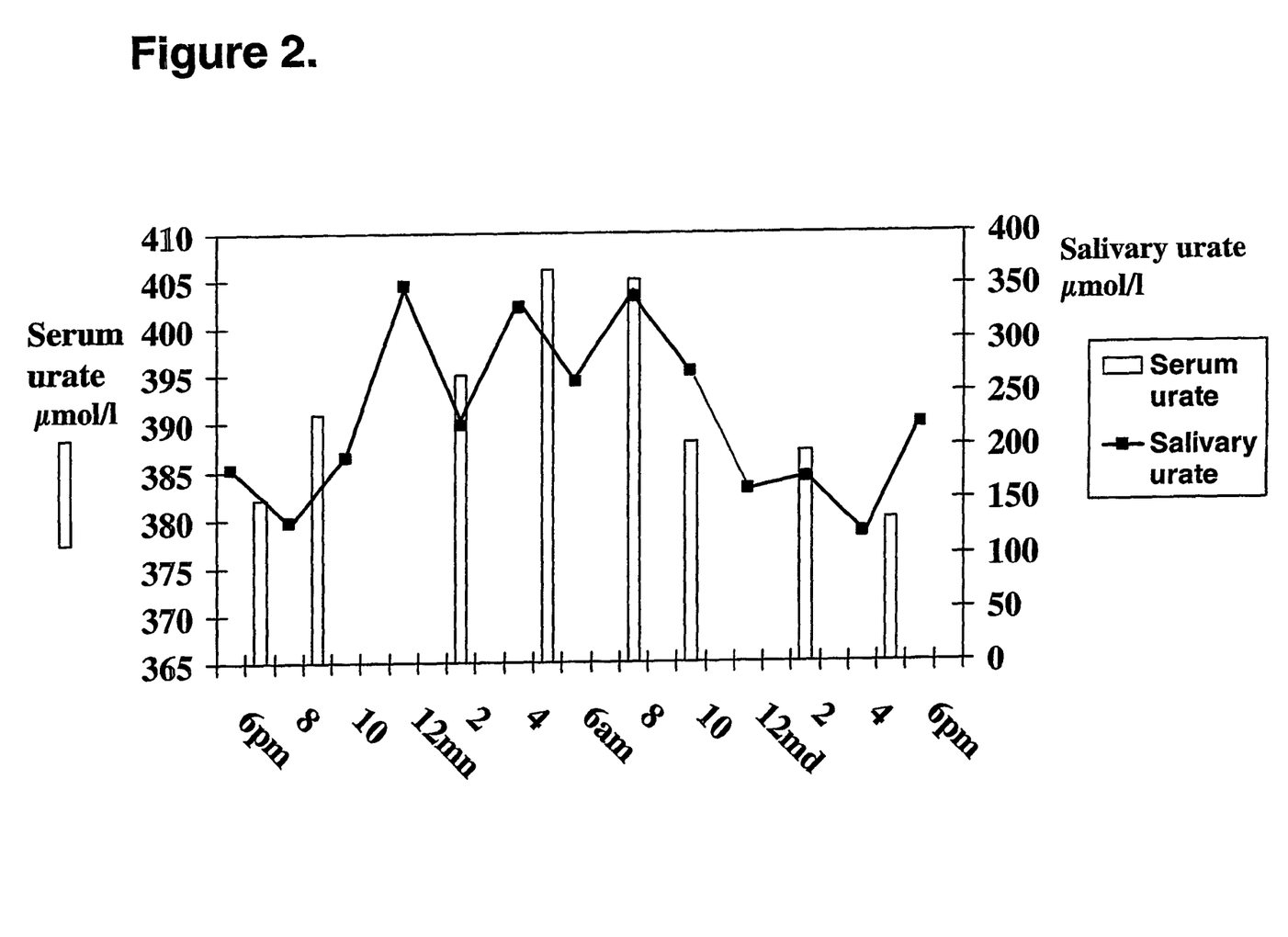
FIG. 2 Showing increased sensitivity and circadian variation of salivary urate concentration as compared with blood urate using serum data from Kanabrocki et al. Salivary urate correlates with serum. Serum urate (bars and left Y axis) ranges from 380-405 μmol/l whilst saliva (line and right Y axis) is amplified from 125-350 μmol/l i.e. a range of 225 μmol/l.
Figure 3:
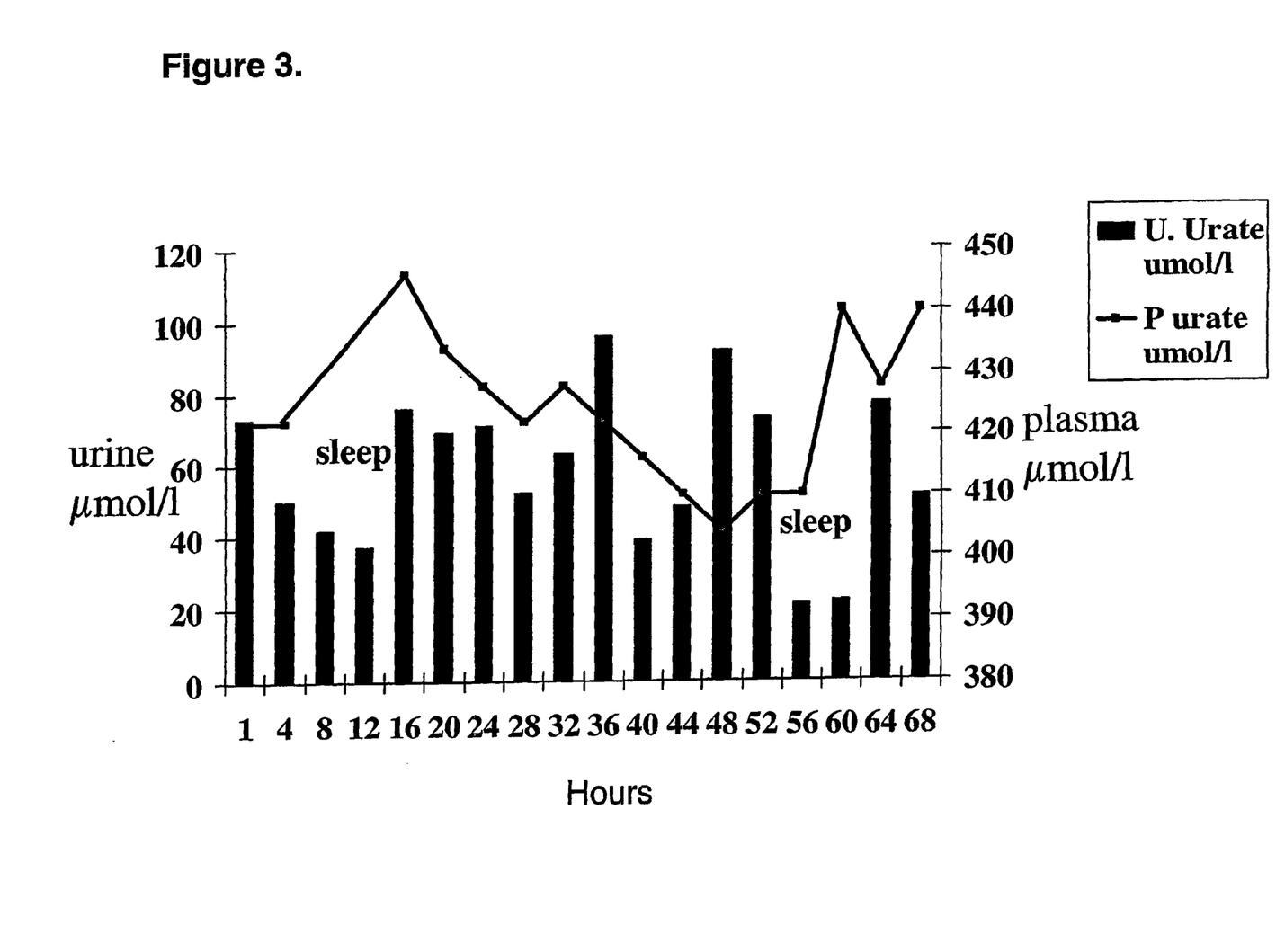
FIG. 3 Showing fall in blood urate during 42 hours of sleep deprivation (while on a low purine diet) with increase during sleep and associated fall in urine uric acid excretion.

However, blood urate is a product of endogenous urate production, diet, renal excretion and gastro-intestinal excretion. In the intestine, urate undergoes bacterial degradation (enteral uricolysis) (Sorensen, 1960) and is subject to diurnal variability (Owen-Smith et al, 1981, FIG. 1). At night, urine excretion of uric acid is reduced whereas intestinal elimination is increased. It has been shown that blood urate concentrations also demonstrate diurnal variation (Kanabrocki et al, 2000, FIG. 2) to a lesser degree. The diurnal variation is thought to be primarily due to sleep (Owen-Smith, 1983. FIG. 3). The net result of these changes is relative stability of blood urate so that with overproduction of cellular urate, increase in blood concentration is delayed.

Urate is a small molecule and widely diffused in extracellular fluid, including saliva. Salivary urate is not reabsorbed (as in the kidney) but is swallowed and degraded by bacteria in the intestine. Thus, rapid changes or surges of urate production are detected in saliva without significant change in blood urate concentration.

It has been demonstrated that the concentration of urate in saliva is a more sensitive indicator of cellular urate metabolism than is found in blood. This was established in patients suffering from gout, before and after treatment with allopurinol (that prevents urate formation) and in normal subjects undertaking exercise or providing samples day and night (to assess diurnal variability in excretion) (Owen-Smith et al, 1998).

Figure 4:
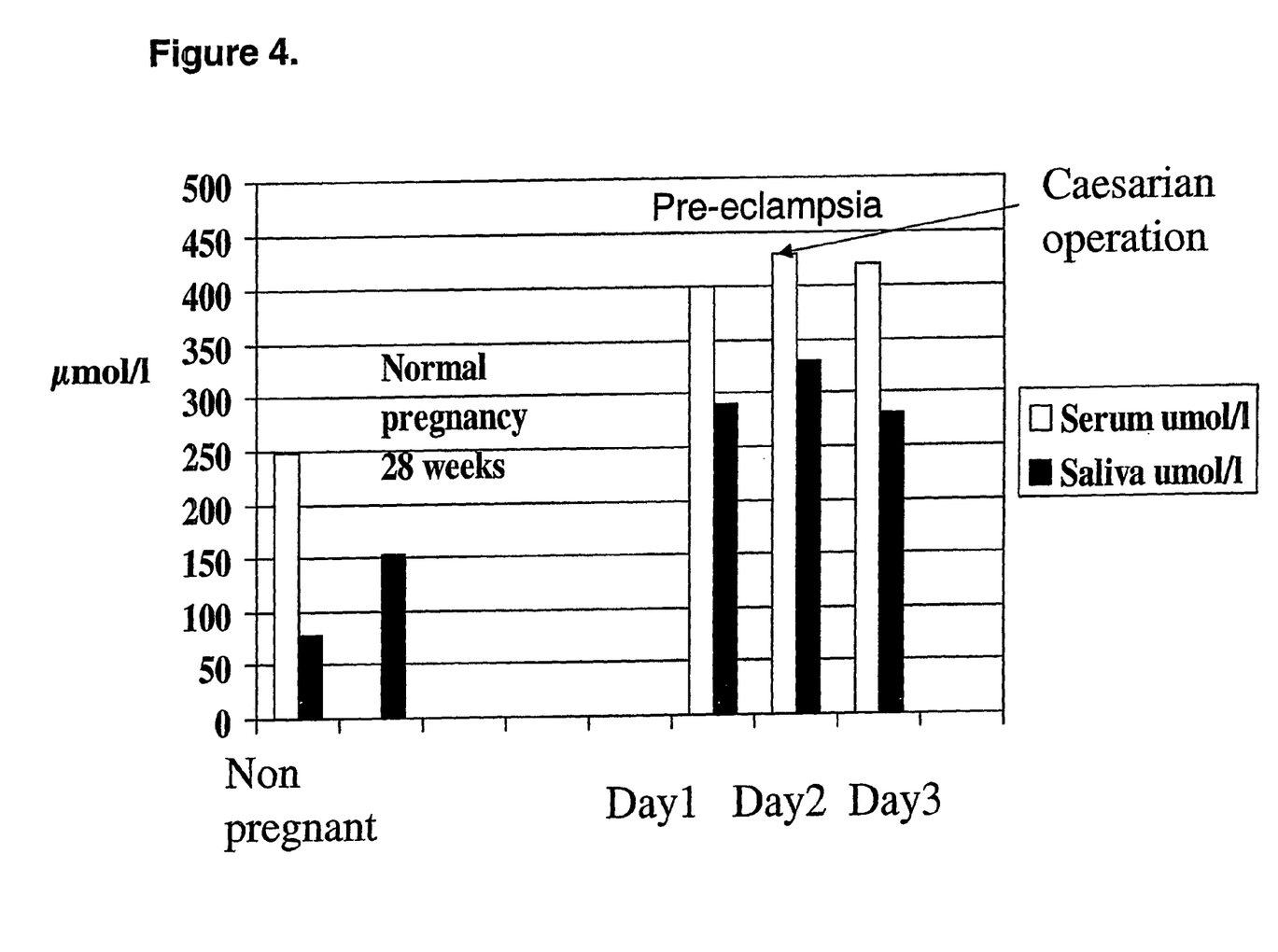
FIG. 4 Blood and saliva data for non pregnant women, a normal pregnancy of 28 weeks and 3 days blood and saliva urate data from a patient with pre-eclampsia, who was delivered on day 2, showing elevations in salivary urate.

Further, a patient with pre-eclampsia provided both blood and salivary urate samples on the days before and after delivery (FIG. 4). Both sets of samples were greatly raised as compared with normal non-pregnant women and a 28 weeks pregnancy. The salivary levels in pre-eclampsia showed good correlation with blood levels. The increase in saliva concentration between the 28 weeks pregnancy to delivery was 180 μmol/l.

According to the present invention there is provided a method for diagnosis of pre-eclampsia which comprises measuring urate in a biological sample. The levels obtained by measuring the levels of urate in pregnant human females may be compared with normal values resulting from measurement of urate levels in biological samples obtained from pregnant females of similar gestational age who did not develop pre-eclampsia.

The sample may comprise whole blood or plasma which may also contain an anticoagulant. However, in a preferred aspect of the invention, the sample is taken from maternal saliva. Maternal salivary urate has not previously been used for diagnosis of pre-eclampsia in pregnancy. Due to diurnal variation in levels of salivary urate, in order to monitor change in urate levels over the duration of pregnancy, the sample should preferably be collected at the same time of day.

Saliva samples may be collected in any suitable manner. For example, a sample of saliva may be collected directly in a tube. Alternatively the sample may be collected in a tube having an insert to take a cotton swab that has a perforation at its base. The cotton swab is moistened under the tongue and then chewed for about 45 seconds to absorb saliva. The collected sample is then refrigerated at under 10° C., preferably 4° C. until it can be transported and processed by a laboratory. The tube may then be centrifuged, for example at 3000 revs for 5 minutes, so that it is ready for assay.

The levels of urate in the biological sample can be measured using any suitable test or biological assay, including a dip stick test, the timed end point method or by means of the dry test method.

The dip stick test comprises using a standard pharmaceutical dip stick used for biological testing which has areas coated with reagents which change colour when urate is detected. The reagents used are those specific for detecting urate in saliva and values obtained may be compared against a standardised colour chart.

Uric acid reagent may be used to measure the uric acid concentration by the timed end point method. Uric acid is oxidised by uricase to produce allantoin and hydrogen peroxide. The hydrogen peroxide reacts with 4-aminoantipyrine (4-AAP) and 3,5-dichloro-2-hydroxybenzene sulfonate (DCHBS) in a reaction catalysed by peroxidase to produce a coloured product.

A commercially available multi-tester, the SYNCHRON CX Systems MULTI Calibrator in which the sample is its own reagent may be used to assay the sample. The change in absorbance at 920 nanometers may then be monitored. This change is directly proportional to the concentration of uric acid in the sample and is used by the SYNCHRON CX System to calculate and express the uric acid concentration. This assay method provides a level of accuracy within +/−5% and allows interpretation within a set of values from 30 μmol/l to 1000 μmol/l.

A dry test method may also be used to assay for urate levels in the saliva sample. A dry multi-layer chemistry film assay can be used in this method. The dry reagents react with the sample to generate a coloured product that appears within a few minutes. The saliva sample is distributed uniformly by spreading and diffuses into the reagent layer where Urate is hydrolysed by uricase to generate hydrogen peroxide. Leuco dye, which changes to a blue colour by oxidation of hydrogen peroxide in the presence of peroxidase, may be used and the colour intensity of the spot can be measured by reflectance photometry. However, any other suitable dye may alternatively be used.

According to a second aspect of the invention there is provided the use of urate levels in the saliva as an indicator of pre-eclampsia.

A third aspect of the invention provides a diagnostic kit for performing the method of any one of the above claims, wherein the kit comprises reagents for the determination of the level of urate in a biological sample. The kit suitably also comprises instructions for the use in a method of the invention.

The reagents of the kit may comprise one or more enzymes and one or more compounds which react to form a chromagen which can be measured spectrophotometrically (or by another suitable method) in order to determine the urate level. The enzyme of the kit may be uricase which converts uric acid into allantoin and hydrogen peroxide. Peroxidase may then be used in a further reaction to result in coupling of the reaction compounds to form the chromagen. The reaction compounds may be selected from 3,5 Dichloro-2-hydroxybenzene-sulfonic acid or 2-hydroxy-3,5-dichlorobenzenesulfonate and 4-aminoantipyrene or 4-aminophenazone. Alternatively any other suitable reagents commonly used in uric acid or urate assays may be used in accordance with the invention.

In a fourth aspect of the invention there is provided test equipment for measuring urate in a biological sample, preferably in saliva, wherein the test equipment comprises reagents for the determination of the level of urate in a biological sample. The reagents of the test equipment are listed above in relation to the third aspect of the invention.

According to a preferred embodiment of the present invention there is provided a method for the diagnosis of pre-eclampsia which comprises the steps of (1) collecting a biological sample from a subject; optionally storing the sample at below 10° C.
(2) processing the biological sample prior to assaying
(3) assaying the sample for the concentration of urate present
(4) comparing the results obtained in (3) with a normal control value in order to reach a diagnosis of pre-eclampsia.

As discussed above, in relation to step (1), the sample may be saliva and can be obtained as described. It can also be processed according to step (2) as described above. If the sample is blood then the sample collection, processing and storage can be suitably adapted in order to assay the plasma component of the sample.

The assay for the concentration of urate according to step (3) in the sample may be as referred to above by any generally convenient method, such as the dry test method, the dipstick test or timed end-point method.

Comparison of the test results in (3) according to step (4) is made with reference to normal values resulting from measurement of urate levels in biological samples from pregnant females of similar gestational age who did not develop pre-eclampsia. An elevated level of urate in the sample under assay in comparison to the normal control is indicative of pre-eclampsia in the patient.

The invention may also diagnose conditions of oxidative stress from other causes in pregnancy and may assess activity or severity of pre-eclampsia.

The invention may also be used as a non-physical and non-chemical non-invasive test of fetal well being. The fetus is only able to excrete urate into the amniotic fluid, which becomes highly concentrated i.e. toxic.

The ease of collection of saliva and assay of urate fulfil the criteria of cost, safety and convenience for patient and laboratory technician.

The invention is a useful adjunct to surveillance of pregnancy and pre-eclampsia.

References herein to urate include uric acid unless the context specifies otherwise. Urate in biological fluids in the body is generally found in the form of the sodium salt of uric acid.

Preferred features of the first aspect are for the second and subsequent aspects mutatis mutandis.

The invention will now be described by example and with reference to the following figures.

SAMPLE COLLECTION

Before cleaning teeth or having a meal the woman removes the cotton wool swab (FIG. 5) (1), from the sterile Salivette® tube (2). A Salivette® is a plastic disposable centrifuge tube with an insert to take a cotton swab that has a perforation at its base. This is not material to the invention but we envisage other methods of saliva sampling and testing to be developed such as dry test stick or dip stick coated with suitable reagents. The woman places the cotton wool swab under the tongue to moisten it and then gently chews upon it for about 45 seconds. This activates salivation within the mouth and the swab absorbs the mixed saliva. The swab is then returned to the insert in the Salivette®, which is appropriately labelled, to ensure safe storage of the sample. It is then kept cool in a normal domestic refrigerator at approximately 4° C. until it is transported and processed by the laboratory.

Sample Assay

Figure 5:
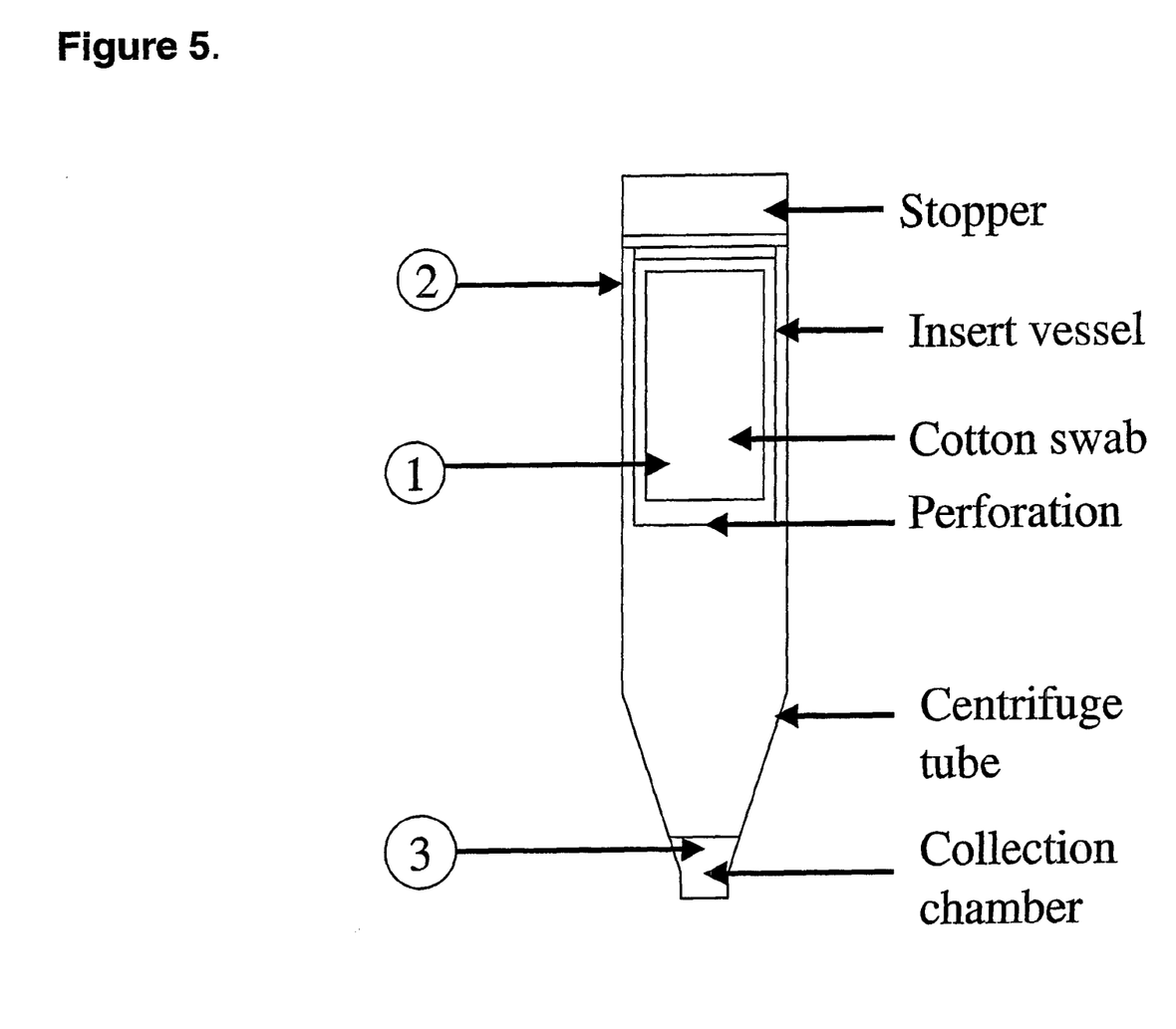
FIG. 5 Showing a plastic capped Salivette® tube and cotton swab insert. Note insert vessel, which has a perforation in its base. From 0.5-1 ml of saliva collects in the apex of the tube after centrifugation.

Upon receipt at the laboratory and after laboratory and patient documentation is collected from the tube label, the Salivette® tube with the swab insert is centrifuged at 3000 revs for 5 minutes. The clear sample of mixed saliva (3) is then ready for assay. Alternatively, the sample can be prepared for assay by compressing the swab insert. Assay may be undertaken by any method that provides a level of accuracy within +/−5% and allow interpretation within a set of values from 30 μmol/l to 1000 μmol/l. However for completeness a method using a commercially available multi-tester, the SYNCHRON CX Systems MULTI Calibrator will now be described.

The sample is its own reagent and in conjunction with the SYNCHRON CX Systems MULTI Calibrator, although intended for the quantitative determination of uric acid (urate) concentration in serum, plasma or urine, saliva is perfectly compatible with this system.

Uric acid reagent is used to measure the uric acid concentration by a timed end point method. Uric acid is oxidised by uricase to produce allantoin and hydrogen peroxide. The hydrogen peroxide reacts with 4-aminoantipyrine (4-AAP) and 3,5-dichloro-2-hydroxybenzene sulfonate (DCHBS) in a reaction catalysed by peroxidase to produce a coloured product.

The Synchron CX System automatically proportions the appropriate sample and reagent volumes into a cuvette. The ratio used is one part sample to 25 parts reagent. The system monitors the change in absorbance at 920 nanometers. This change in absorbance is directly proportional to the concentration of uric acid in the sample and is used by the Synchron CX System to calculate and express the uric acid concentration.

EXAMPLES

In the assessment of sensitivity of salivary urate as compared with blood (FIG. 2) the results of 2 hourly urate concentrations over 24 hours were compared with the serum urate data of Kanabrocki et al. Salivary urate was correlated with the diurnal variation of serum urate, increased at night. The 24-hour range for serum was from 380 μmol/l to 405 μmol/l i.e. a variation of only 25 μmol/l whilst the results for saliva were amplified from 125 μmol/l to 350 μmol/l i.e. a range of 225 μmol/l.

Figure 6:
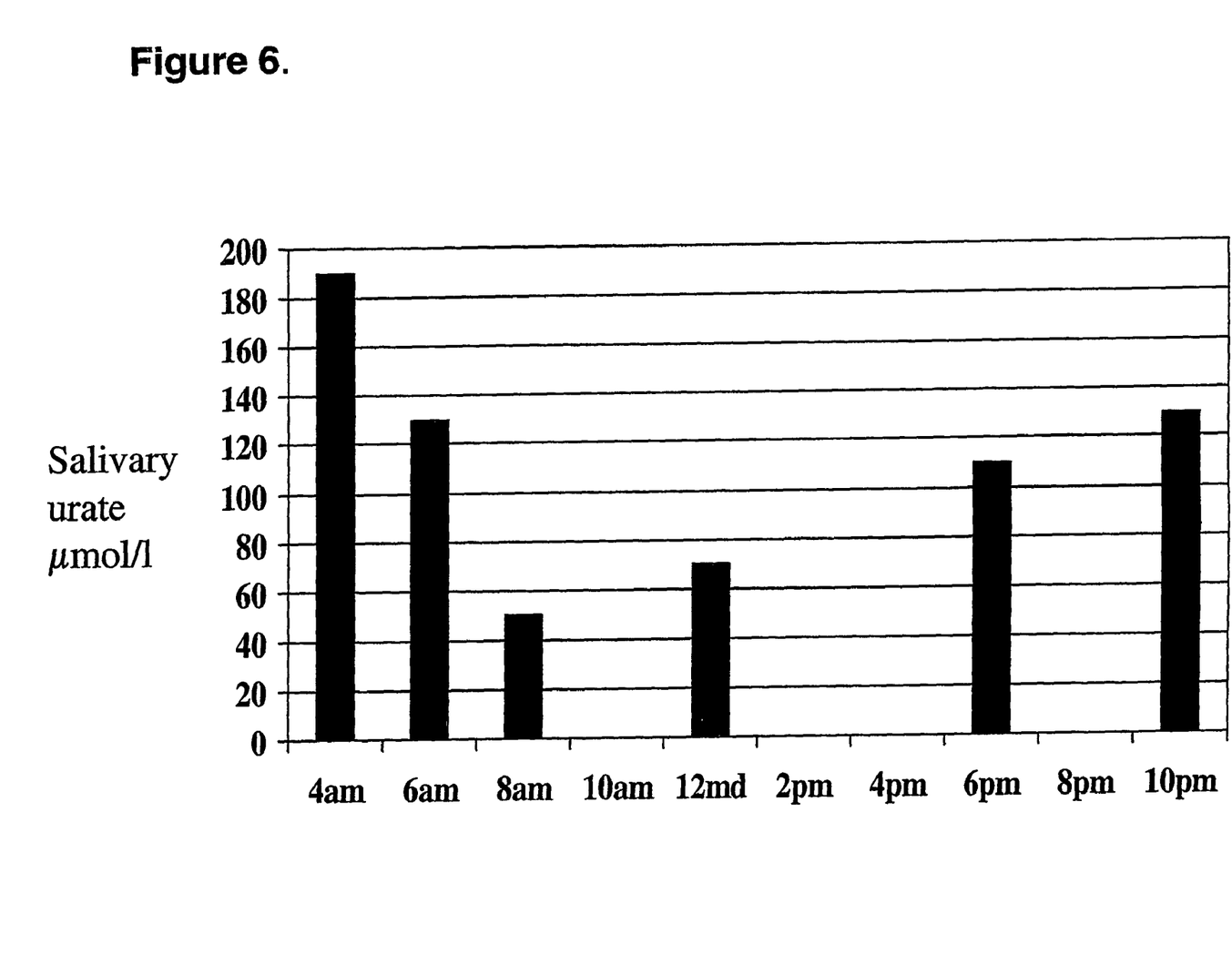
FIG. 6 Showing mean normal diurnal variation of salivary urate in 4 non-pregnant females. The variation ranges from 70-190 μmol/l.

Four non-pregnant women (FIG. 6) gave salivary urate samples to demonstrate diurnal variation. There was increase in the early hours. This must be taken into consideration in interpretation of test results and also changes in normal variation due to pregnancy. The average of the 8 am to 6 pm test results (76 μmol/l) show a significant lower value set than the pre-eclamptic (325 μmol/l) (FIG. 4).

A routine antenatal clinic survey of urate levels was carried out comprising 149 random single samples from 148 patients. The average age of the patients was 27 years and the average gestation was 31 weeks. The mean salivary urate level was 179 μmol/l SD 84 μmol/l. Salivary urate levels were found to increase with gestational age. 23 patients had serum urate levels available for comparison (salivary urate M±SD 180±50, serum urate 249±55). Thus, salivary urate levels were approximately 70% of the blood level during pregnancy and salivary urate level of 250 μmol/l is equivalent to the upper limit of normal in blood for women of 360 μmol/l. The result of the antenatal clinic survey was surprising since salivary urate is affected by a variety of physiopathological factors apart from pregnancy. This is demonstrated by a small resting sample at 20 weeks after ultrasound scan. One patient with twins at 28 weeks was shown to have an abnormal test before blood tests, ultrasound and early delivery were carried out.

An inpatient study of patients admitted for observation of hypertension or treatment of pre-eclampsia was compared with 'normal' controls. 37 sample sets of salivary urate were taken at 8 am, 12 md, 4 pm, 8 pm, 12 mn and 4 am. In pre-eclampsia, increase in salivary urate occurred throughout the day which suggests increased maternal urate production, renal retention and increased fetal amniotic fluid urate concentration. In one severe case of pre-eclampsia the salivary urate level was greater than the blood level.

REFERENCES

Many A., Hubel C A., Roberts J M. (1996) Hyperuricaemia and xanthine oxidase in preeclampsia, revisited. American Journal of Obstetrics and Gynaecology 174(1), 288-291

Chappell L C., Seed P T., Briley A L., Kelly F J., Hunt B J., J H., Charnock-Jones S., Mallet A I., Poston L (2002). A longitudinal study of biochemical variables in women at risk of preeclampsia. American Journal of Obstetrics and Gynaecology, 186, 127-136.

Sorensen L B. The elimination of uric acid in man studied by means of $C^{14}$-labelled uric acid (1960) Scandinavian Journal of Clinical Laboratory Investigation; supplement 54.

Owen-Smith B D, & Whyman A. (1981). Diurnal and nocturnal variations of enteral uricolysis during fasting and refeeding. (Abstract) Annals of Rheumatic Diseases, 40, 523-524.

Kanabrocki E L., Third J., Ryan M D., Nemchausky B A., Shirazi P., Scheving L E., Hines E Jr., McCormick J B (2000) Circadian relationships of serum uric acid and nitric oxide. Journal of the American Medical Association; 283, 2240-2241.

Owen-Smith B D (1983). Significance of variations of uric acid elimination Annals of Rheumatic Diseases; 42, Supplement p 87.

Owen-Smith B D., Quiney, J & Read J (1998). Salivary urate in gout, exercise and diurnal variation. Lancet; 351:1932

The invention claimed is:

1. A method for diagnosis of pre-eclampsia which comprises:
   a) collecting a sample of maternal saliva from a subject;
   b) processing the sample prior to assaying;
   c) assaying the sample for the concentration or urate present; and
   d) comparing the results obtained in c) with a normal control value, thereby diagnosing pre-eclampsia.

2. A method as claimed in claim 1, wherein the urate is measured by means of a timed end point method.

3. A method as claimed in claim 1, wherein the urate is measured by means of a dry test method.

4. A method as claimed in claim 1, wherein the urate is measured by means of a dip stick method.

* * * * *